US00RE36582E

United States Patent [19]

Furuya et al.

[11] E Patent Number: Re. 36,582

[45] **Reissued Date of Patent: *Feb. 22, 2000**

[54] PHOTOGRAPHING LIGHT QUANTITY CONTROLLER FOR ENDOSCOPE

[75] Inventors: Katsuhiko Furuya; Masaaki Nakasima; Takayuki Enomoto; Tadashi Takahashi, all of Tokyo, Japan

[73] Assignee: Asahi Kogaku Kogyo Kabushiki Kaisha, Tokyo, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/763,347

[22] Filed: Dec. 11, 1996

Related U.S. Patent Documents

Reissue of:

[64] Patent No.: 5,191,369
Issued: Mar. 2, 1993
Appl. No.: 07/748,026
Filed: Aug. 21, 1991

U.S. Applications:

[63] Continuation of application No. 08/395,927, Feb. 28, 1995, abandoned.

[30] Foreign Application Priority Data

Aug. 31, 1990 [JP] Japan ..... 2-231361

[51] Int. Cl.[7] ..... G03B 29/00

[52] U.S. Cl. ..... 396/17; 396/159; 362/4

[58] Field of Search ..... 396/14, 17; 362/4, 362/5, 276; 355/68, 69, 71

[56] References Cited

U.S. PATENT DOCUMENTS

| | | | |
|---|---|---|---|
| 3,599,630 | 8/1971 | Sato et al. | 354/62 X |
| 4,249,809 | 2/1981 | Kanemaru et al. | 354/458 |
| 4,524,761 | 6/1985 | Hattori et al. | 354/62 X |
| 5,115,261 | 5/1992 | Noda et al. | 354/62 |
| 5,159,380 | 10/1992 | Furuya et al. | 354/62 X |
| 5,184,159 | 2/1993 | Furuya et al. | 354/52 |
| 5,184,170 | 2/1993 | Takahashi et al. | 354/62 X |

FOREIGN PATENT DOCUMENTS

| | | |
|---|---|---|
| 0039458 | 11/1981 | European Pat. Off. . |
| 53-036980 | 4/1978 | Japan . |
| 54-132380 | 10/1979 | Japan . |
| 58-075526 | 5/1983 | Japan . |
| 61-013236 | 1/1986 | Japan . |
| 2-084609 | 3/1990 | Japan . |

OTHER PUBLICATIONS

English Abstract of Japanese Patent 61–13236.
English Abstract of Japanese Patent 2–84609.

*Primary Examiner*—Howard B. Blankenship
*Attorney, Agent, or Firm*—Greenblum & Bernstein, P.L.C.

[57] ABSTRACT

A photographing light quantity controller for an endoscope, which is used to control the quantity of illuminating light when a photograph is to be taken through the endoscope. The photographing light quantity controller comprises a device for supplying light for illuminating an object to the endoscope, a device for detecting a quantity of light that is reflected from the object and for outputting a signal in accordance with the detected quantity of light, and a device for amplifying the signal, with the amplifying device having a plurality of amplification factors which can be selected as desired. A photographing light quantity control device is provided for controlling the quantity of illuminating light that is supplied to the endoscope when a photographing operation is conducted, on the basis of the output signal from the amplifying device. A device is also provided for automatically switching over the amplification factors of the amplifying device from one to another in accordance with the brightness of the object.

26 Claims, 14 Drawing Sheets

FIG. 2

| EXPOSURE IND. EI | 0 | 1 | 2 | 3 | 4 | 5 | 6 | 7 | 8 | 9 |
|---|---|---|---|---|---|---|---|---|---|---|
| EXPOSURE QUANTITY (RELATIVE VALUE) | $2^{\frac{5}{2}}$ | $2^{2}$ | $2^{\frac{3}{2}}$ | $2^{1}$ | $2^{\frac{1}{2}}$ | 1 | $2^{-\frac{1}{2}}$ | $2^{-1}$ | $2^{-\frac{3}{2}}$ | $2^{-2}$ |

FIG. 3

| BRIGHTNESS INDEX BI | 0 | 1 | 2 | 3 | 4 | 5 | 6 | 7 | 8 | 9 |
|---|---|---|---|---|---|---|---|---|---|---|
| BRIGHTNESS (RELATIVE VALUE) | $2^{-\frac{5}{2}}$ | $2^{-2}$ | $2^{-\frac{3}{2}}$ | $2^{-1}$ | $2^{-\frac{1}{2}}$ | 1 | $2^{\frac{1}{2}}$ | $2^{1}$ | $2^{\frac{3}{2}}$ | $2^{2}$ |

PHOTOGRAPHING LIGHT QUANTITY CONTROLLER FOR ENDOSCOPE

Matter enclosed in heavy brackets [ ] appears in the original patent but forms no part of this reissue specification; matter printed in italics indicates the additions made by reissue.

*This application is a continuation of application Ser. No. 08/395,927, filed Feb. 28, 1995, now abandoned, which is a Reissue application of U.S. Pat. No. 5,191,369.*

BACKGROUND OF THE INVENTION

The present disclosure relates to subject matter contained in Japanese Patent Application No. 2-231361 (filed on Aug. 31, 1990), which is expressly incorporated herein by reference in its entirety.

FIELD OF THE INVENTION

The present invention relates to a photographing light quantity controller for an endoscope, which is used to control the quantity of illuminating light when a photograph is to be taken through the endoscope.

Endoscopes are generally designed to be capable of not only observing the inside of a hollow organ in the patient's body but also taking a photograph of it.

DESCRIPTION OF THE PRIOR ART

In a typical conventional photographing light quantity controller for an endoscope, reflected light from an object, that is illuminated by a light source, is received and converted into an electric signal with a light-receiving element. The output of the light-receiving element is integrated to obtain an integral value. When the integral value reaches a preset reference voltage, the application of the illuminating light to the object is stopped, thus effecting automatic control of the photographing light quantity.

However, since the output signal (voltage) from the light-receiving element is weak, the output voltage is inputted to a photographing light quantity control circuit after being amplified in an amplifier circuit.

A typical conventional amplifier circuit that is employed for this purpose is designed to amplify the input voltage with a fixed amplification factor. Therefore, after a synchro switch is turned on to initiate a photographing operation, the amplifier circuit amplifies the output voltage from the light-receiving element with a constant amplification factor at all times and inputs the amplified voltage to the photographing light quantity control circuit.

Since the object of an endoscope is illuminated with light that is supplied to the endoscope from a light source, the brightness of the object varies in inverse proportion to the square of the distance between the object and the endoscope. Moreover, the object distance range is wide, i.e., from about 5 mm to 10 cm or more, even in a normal use.

Accordingly, when the object is distant and dark, the voltage that is inputted to the photographing light quantity control circuit is considerably low, so that the voltage value may be inaccurate and the signal processing executed in the photographing light quantity control circuit takes a great deal of time. Consequently, the illuminating light quantity control cannot accurately be effected.

In particular, a large error may be produced in a control system wherein an exposure time is predicted from the rate of change of the integral value per unit time (differential with respect to time), immediately after the initiation of an exposure operation.

SUMMARY OF THE INVENTION

An object of the present invention is to provide a photographing light quantity controller for an endoscope, which is capable of accurate, illuminating light quantity control, even when the brightness of the object is remarkably low.

Other objects and advantages of the present invention will become apparent from the following detailed description of illustrated embodiments of the invention.

According to the present invention, there is provided a photographing light quantity controller for an endoscope, which is used to control the quantity of illuminating light when a photograph is to be taken through the endoscope. The photographing light quantity controller comprises a device for supplying light for illuminating an object to the endoscope; a device for photographing the object; a photoelectric conversion device for converting a brightness level of light that is reflected from the object into an electric signal; a device for integrating the output from the photoelectric conversion device and outputting the resulting integral value; a device for amplifying the output value from the integrating device, with the amplifying device having a plurality of amplification factors which can be selected as desired; a photographing light quantity control device for controlling the quantity of illuminating light that is supplied to the endoscope when a photographing operation is conducted, on the basis of the output signal from the amplifying device; a switch for initiating the photographing operation of the photographing device and the control operation of the photographing light quantity control device; and a device for automatically switching over the amplification factors of the amplifying device from one to another in accordance with the brightness of the object.

BRIEF DESCRIPTION OF THE DRAWINGS

The present invention may be more fully understood from the description of the preferred embodiments of the invention set forth below, together with the accompanying drawings, in which:

FIG. 2 is a chart showing one example of the setting of exposure indexes;

FIG. 3 is a chart showing one example of the setting of brightness indexes;

DESCRIPTION OF THE EMBODIMENTS

Figure 1:
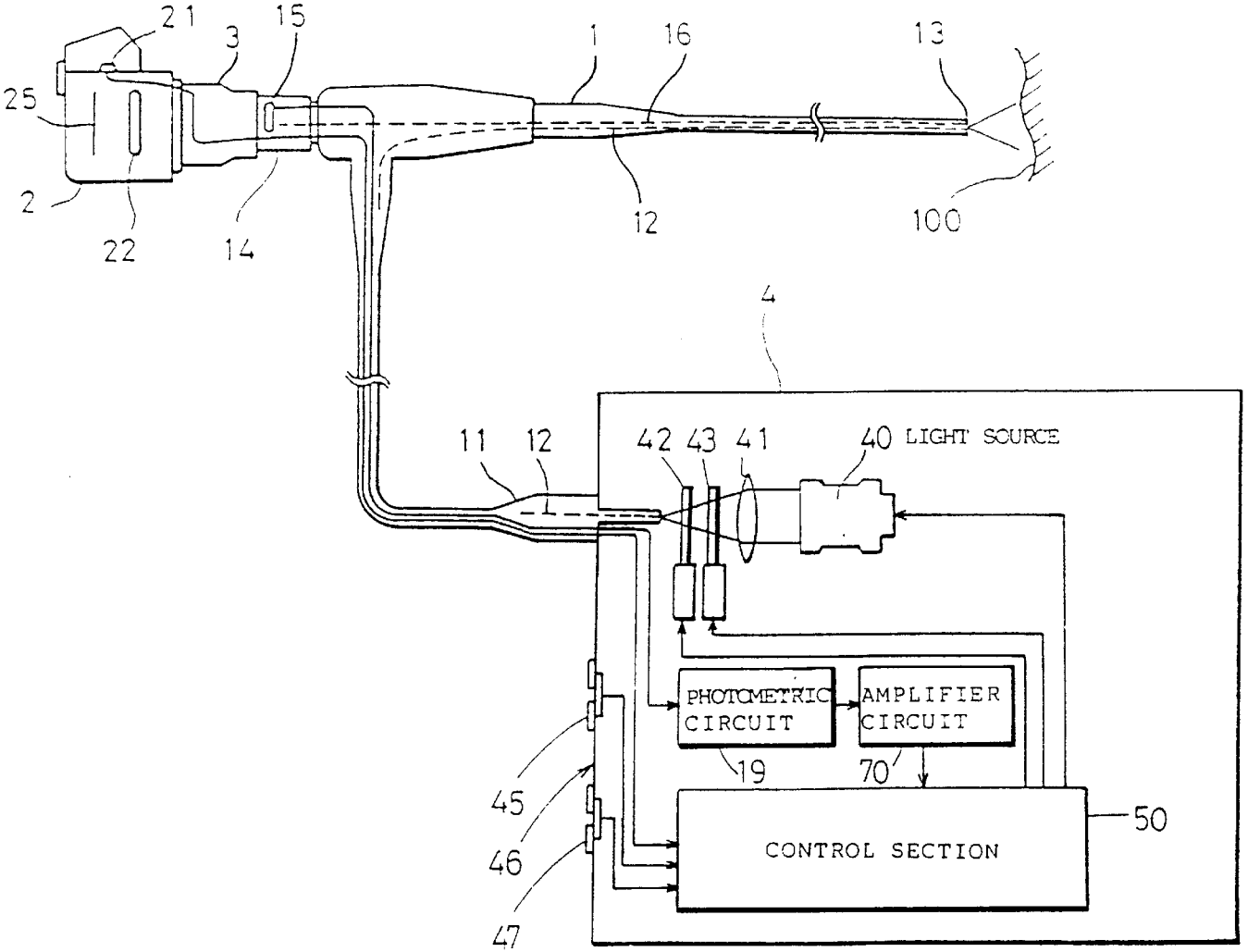
FIG. 1 is a schematic view showing the whole arrangement of one embodiment of the present invention.

Referring to FIG. 1, which shows the whole arrangement of one embodiment of the present invention, reference numeral 1 denotes an endoscope. A camera (photographing device) 2 is detachably attached to an eye-piece 14 of the endoscope 1 through a photographic adapter 3.

Reference numeral 4 denotes a light source apparatus, to which is detachably connected a connector 11 of the endoscope 1. Illuminating light, that is emitted from a light source (lamp) 40, is condensed through a condenser lens 41 so as to be made incident on a light guide fiber bundle 12 in the endoscope 1.

In an illuminating light path, which extends between the light source 40 and the light guide fiber bundle 12, are provided a shutter (light source shutter) 42 which can be opened and closed to fully open and close the illuminating light path, and a variable diaphragm 43 which is capable of varying the area of passage of the illuminating light.

The illuminating light is transmitted through the light guide fiber bundle 12 and applied to an object 100 from the distal end 13 of an insert part of the endoscope 1. The reflected light from the object 100 is transmitted through an image guide fiber bundle 16 to expose the plane (photographic plane) of a film 25 in the camera 2. A shutter 22 in the camera 2 is opened for a predetermined time (e.g., 0.25 sec) only when a synchro switch 21 is turned on.

A light-receiving element 15 is provided in the eye-piece 14 to convert a brightness level of the exposure light that is applied to the plane of the film 25 into an electric signal. The output voltage from the light-receiving element 15 is integrated in a photometric (integration) circuit 19, and an integral value is outputted from the photometric circuit 19. The output signal (voltage value) from the photometric circuit 19 is inputted to a control section 50 after being amplified in an amplifier circuit 70.

The photometric circuit 19 may be provided in either the light source apparatus 4 or the endoscope 1.

An exposure index setting switch 45 is provided on an operation panel 46 that is attached to the surface of the light source apparatus 4 to set an exposure index E1 that determines a quantity of light which is to be applied to the photographic plane 25 in the camera 2. More specifically, the exposure index setting switch 45 is arranged such that the exposure quantity can be controlled in units of 0.5 on the EV exponential valve scale, as shown exemplarily in FIG. 2.

A brightness index setting switch 47 is used to set a brightness level of illuminating light that is supplied to the endoscope 1 when used in an observation state. More specifically, the brightness index setting switch 47 enables the brightness level of illuminating light (i.e., the illuminating light flux that is supplied to the endoscope) during the observation to be controlled by use of the brightness index BI set in units of 0.5 on the EV scale, as shown exemplarily in FIG. 3.

Reference numeral 50 denotes a control section which incorporates a microcomputer.

Figure 4:
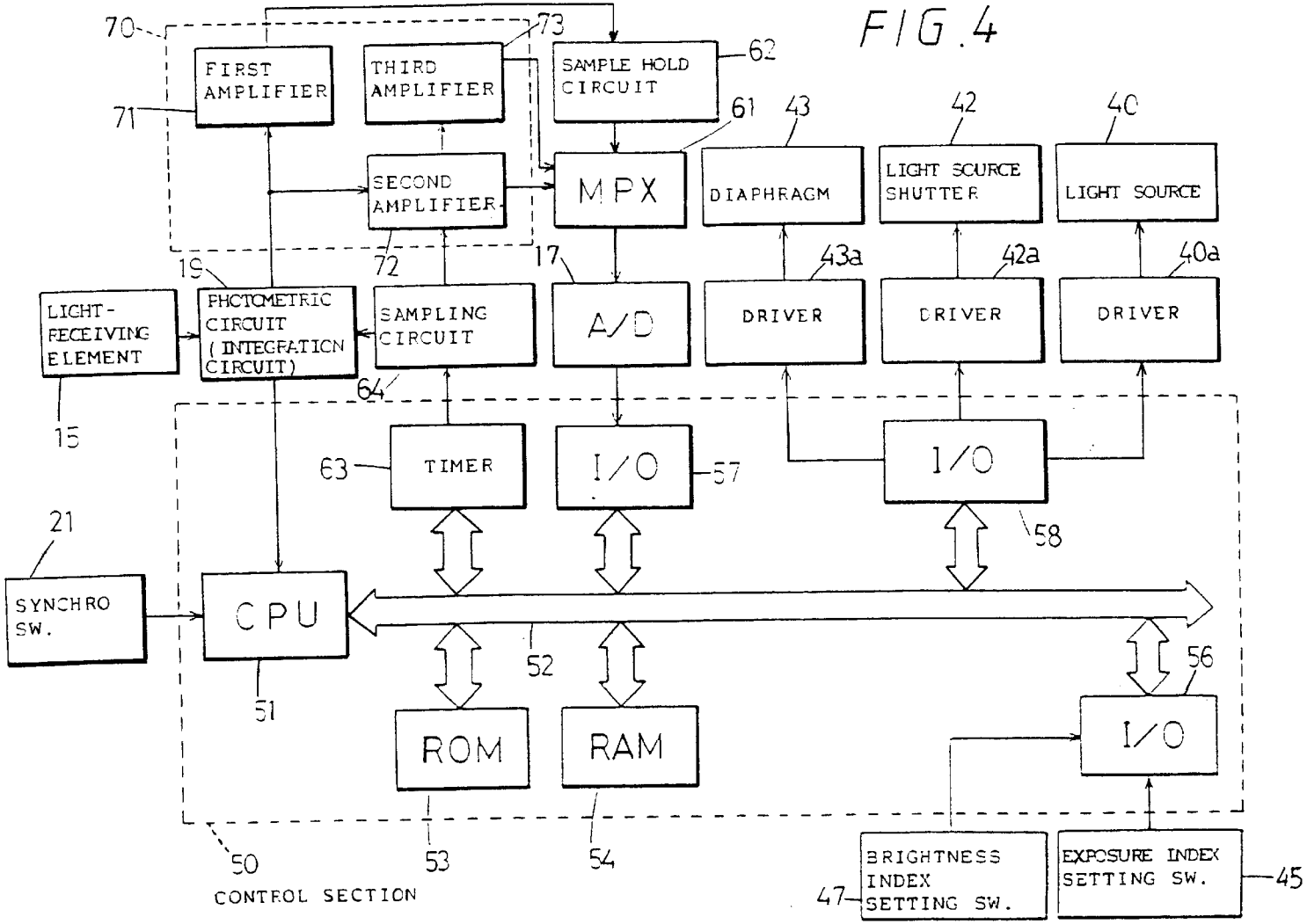
FIG. 4 is a circuit block diagram of the embodiment.

FIG. 4 is a block diagram showing the electrical arrangement of this embodiment. The control section 50 includes a central processing unit (CPU) 51, and a read only memory (ROM) 53 and a random access memory (RAM) 54. A system bus 52 connects the CPU 51 to the Rom 53 and the Ram 54. The CPU 51 is supplied with an interrupt signal which is outputted from the synchro switch 21.

The system bus 52 is further connected with first to third input/output ports 56, 57 and 58. The exposure index setting switch 45 and the brightness index setting switch 47 are connected to the input terminal of the first input/output port 56.

The output from the light-receiving element 15 is integrated in the photometric (integration) circuit 19 to obtain an integral value (integral output voltage V), which is inputted to the amplifier circuit 70. The amplifier circuit 70 comprises a first amplifier 71, a second amplifier 72 and a third amplifier 73, wherein the output from the photometric circuit 19 is inputted to the first and second amplifiers 71 and 72. The amplified output from the first amplifier 71 is inputted to a multiplexer 61 via a sample-and-hold circuit 62.

On the other hand, the amplified output from the second amplifier 72 is inputted to the multiplexer 61 through two routes, that is, one that leads the output directly to the multiplexer 61, and the other that leads the output to the multiplexer 61 via the third amplifier 73 where it is further amplified.

At the time of observation, the peak value of the output signal, that is sampled in the sample-and-hold circuit 62, is selected in the multiplexer 61, and the output from the multiplexer 61 is sent to the second input/output port 57 after being converted into a digital signal in an analog-to-digital converter 17.

At the time of photographing, the output signal from either one of the second and third amplifiers 72 and 73 is selected in the multiplexer 61 and similarly sent to the second input/output port 57 via the analog-to-digital converter 17.

A clock signal that is outputted from a timer 63 that is connected to the system bus 52 is inputted to a sampling circuit 64, so that a sampling pulse is outputted from the sampling circuit 64 to the photometric circuit 19 at a predetermined period, in synchronism, with the clock signal. During the observation, when the sampling pulse is at a low level, the photometric circuit 19 performs an integrated operation, whereas, when the sampling pulse is at a high level, the integral output is zero (i.e., V=0). The sample frequency is set, for example, at about 500Hz, that is, the integration time is shorter than the exposure time.

The output terminal of the third input/output port 58 is connected to drivers 40a, 42a and 43a which control the brightness of light that is emitted from the light source 40, the opening and closing operation of the light source shutter 42, and the degree of opening of the variable diaphragm 43, respectively.

Figure 5:
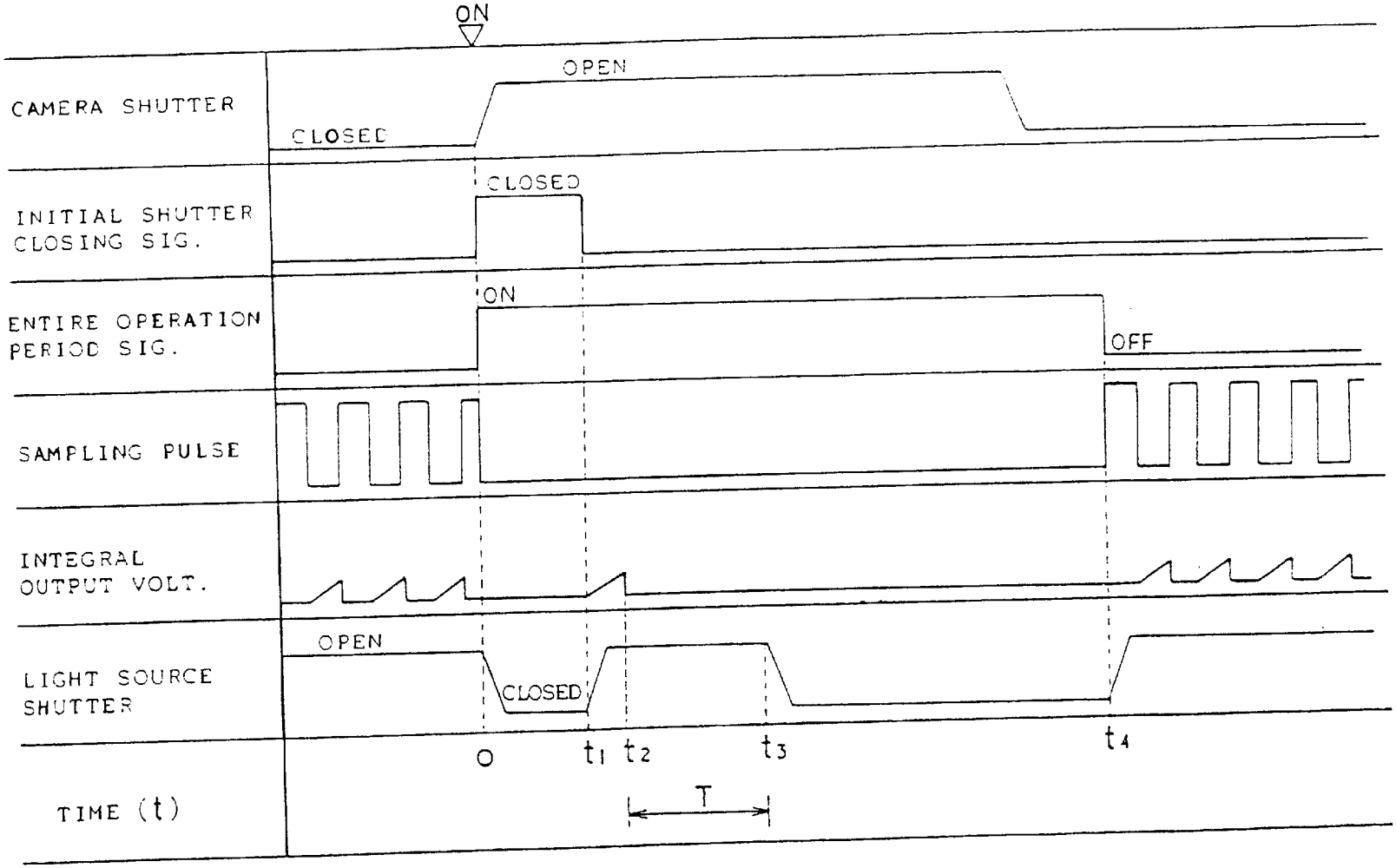
FIG. 5 is a time chart showing the operation of the embodiment.

FIG. 5 is a time chart showing the operation of this embodiment.

When the synchro switch 21 on the camera 2 is turned on, the shutter (camera shutter) 22 in the camera 2 is opened and is closed after a predetermined time (e.g., 0.25 sec) has elapsed. Meantime, the light source shutter 42 in the light source apparatus 4 is temporarily closed at the same time as the synchro switch 21 is turned on. After a predetermined short time (the initial shutter closing time $t_1$) has elapsed, the light source shutter 42 is opened again in order to emit illuminating light for photographing. The initial shutter closing time $t_1$ is, for example, 0.035 sec.

Before the synchro switch 21 of the camera 2 is turned on, that is, during the observation, every time the sampling pulse is at the low level, the output voltage from the light-receiving element 15 is integrated, and the peak value of the integral output voltage that is passed through the first amplifier 71 and the sample-and-hold circuit 62 is selected in the multiplexer 61 and inputted to the CPU 51.

After the light source shutter 42 has been opened, to expose the film plane 25, and the time $t_2$ has elapsed since the turning on of the synchro switch 21, the rate of change of the integral output voltage V per unit time (i.e., differential with respect to time) dV/dt so far is obtained. Assuming that ΔV is the integral output voltage V at the time $t_2$, $$dV/dt=(1/a)\cdot C\cdot \Delta V/(t_2-t_1)$$

where a is an amplification factor in the amplifier circuit 70, and C is a correction coefficient.

The predicted exposure time T, remaining after $t_2$ has elapsed, is obtained as follows:

$$T=(Vr-\Delta V/a)\cdot dt/dV$$

where Vr a reference voltage.

Before the remaining predicted exposure time T is obtained in this way, it is determined which of the output signals from the second and third amplifiers 72 and 73 is to be employed for the calculation.

The reason for this is to avoid the problem that values which are obtained by calculating dV/dt, according to the above equation, involve large errors and are therefore unreliable unless ΔV is greater than a certain value and the problem that, if ΔV is excessively large, the load that is applied to electronic elements, such as the analog-to-digital converter 17, exceeds the maximum input ratings, causing destruction of the electronic elements.

More specifically, when the exposure index EI is large (i.e., when the reference voltage Vr is low), it is preferable to lower the brightness level of the illuminating light. In such a case, dV/dt must be calculated with a small integral output voltage V. At this time, therefore, the output (hereinafter referred to as "H") from the third amplifier 73 is selected in the multiplexer 61 in order to increase the amplification factor. When the brightness index BI is large (i.e., when the brightness level of the illuminating light supplied to the endoscope 1 from the light source apparatus 4 during the observation is high), the object 100 is considered to be distant and rather dark. Therefore, at this time also, the output H from the third amplifier 73 is selected in the multiplexer 61.

Thus, it is possible to obtain precise dV/dt within a short period of time and effect accurate exposure control.

In cases contrary to the above, the output (hereinafter referred to as "L") from the second amplifier 72, with a relatively low amplification factor, is selected.

When numerical values such as those shown in FIGS. 2 and 3 are employed, the above-described selection judgement may be made by setting k in the following equations at k=15, for example:

When EI+BI≧k, H is selected; and

When EI+BI<k, L is selected.

For H, the amplification factor is, for example, from 3 to 4, and for L, for example, from 1 to 2.

After dV/dt is obtained, the output to the analog-to-digital converter 17 is cut off by the multiplexer 61. The reason for this is to prevent the analog-to-digital converter 17 from being fed with a voltage that exceeds the maximum input rating thereof.

When the predicted exposure time T has elapsed, the light source shutter 42 is closed again. When the entire operation terminating time $t_4$ (e.g., 0.5 sec) has elapsed since the turning on of the synchro switch 21, all the elements of the system return to the previous state, i.e., the state before the turning on of the synchro switch 21. Thus, the light source shutter 42 opens again to provide an observation state.

Figure 6:
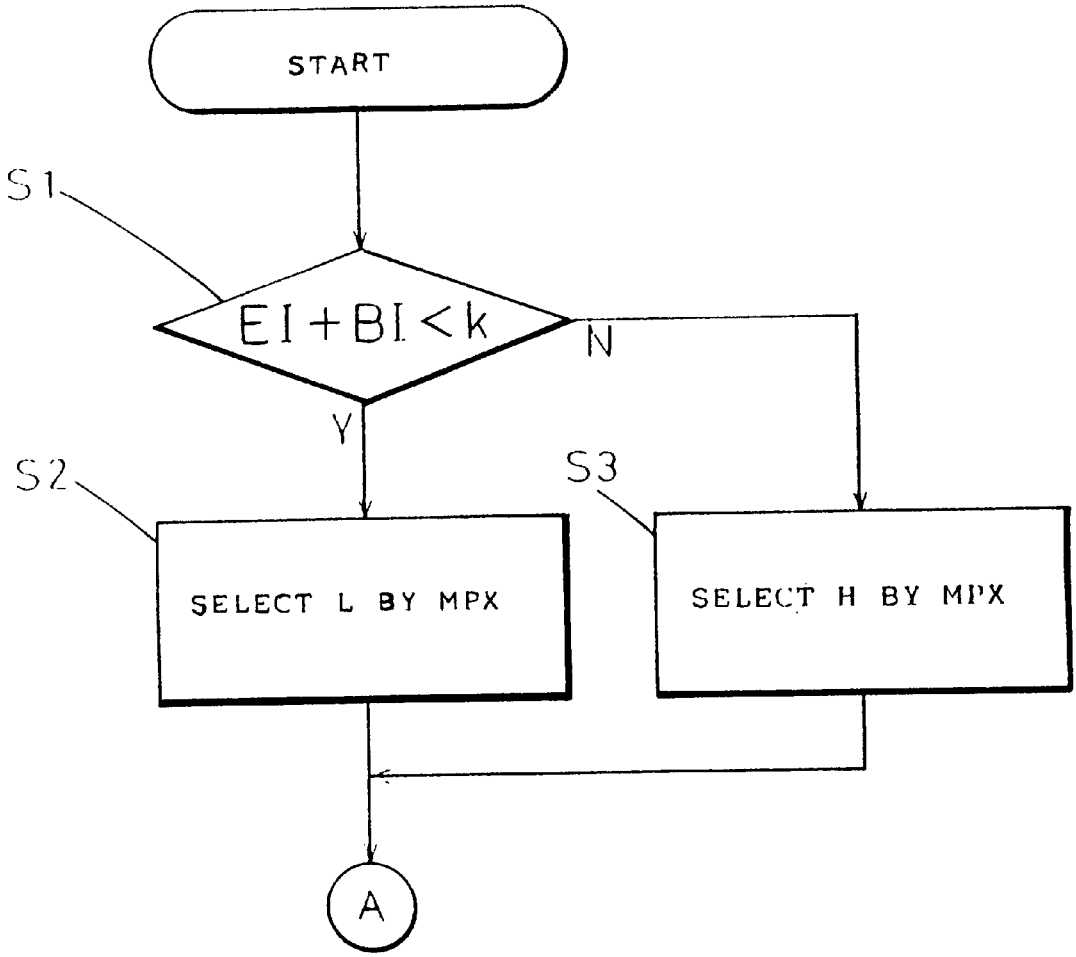
FIGS. 6 and 7 are flowcharts showing a control process in the embodiment.
Figure 7:
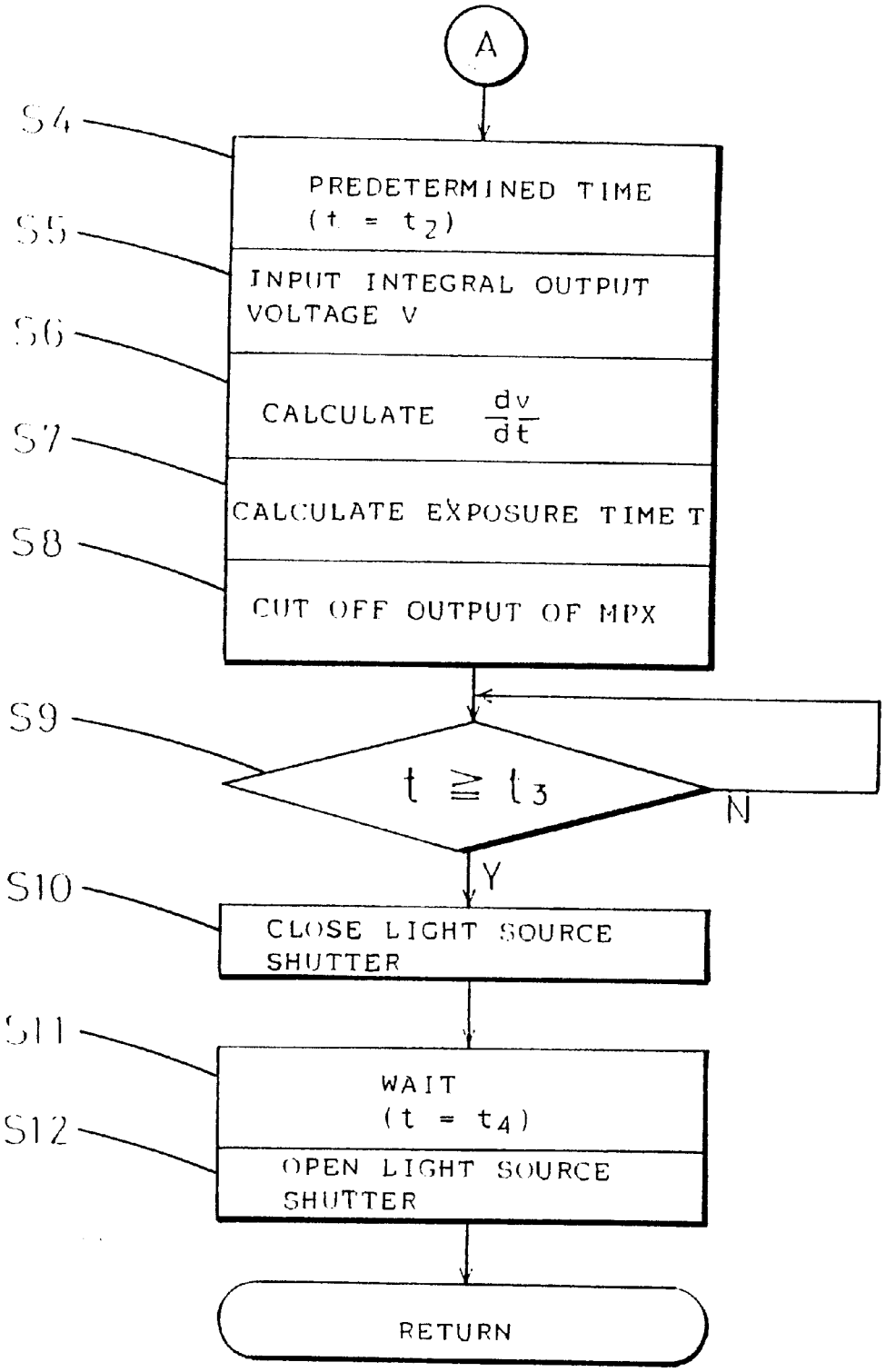

FIGS. 6 and 7 are flowcharts showing a process that is executed by software stored in the ROM 53 to effect the above-described control operation. In the figures, S denotes Steps.

This process is initiated when the synchro switch 21 is turned on. First, EI+BI is compared with a predetermined value k at S1. When EI+BI is smaller than k, the output L from the second amplifier 72 is selected in the multiplexer 61 at S2. When EI+BI is not smaller than k, the output H from the third amplifier 73 is selected in the multiplexer 61 at S3.

In this way, the amplification factor that is employed in the amplifier circuit 70 is automatically switched over from one to another after the synchro switch 21 is turned on.

Next, the elapse of a predetermined value $t_2$ is awaited at S4, the integral output voltage V is inputted at S5, and dV/dt is calculated at S6.

Then, the remaining predicted exposure time T is calculated on the basis of the value of dV/dt at S7, and the output of the multiplexer 61 is cut off at S8.

Next, when it is detected at S9 that the predicted exposure time T has reached the time $t_3$, the light source shutter 42 closed at S10. Then, the elapse of the entire operation terminating time $t_4$ is awaited at S11, and the light source shutter 42 is opened again at S12 to return to the previous observation state.

It should be noted that the way of switching the amplifier circuit in the present invention is not necessarily limited to the foregoing embodiment and that it may be carried out in various other forms.

Other forms of switching the amplifier circuit in the present invention will be explained below. In the following, description of portions or elements that perform the same operations as in the above-described embodiments is omitted.

Figure 8:
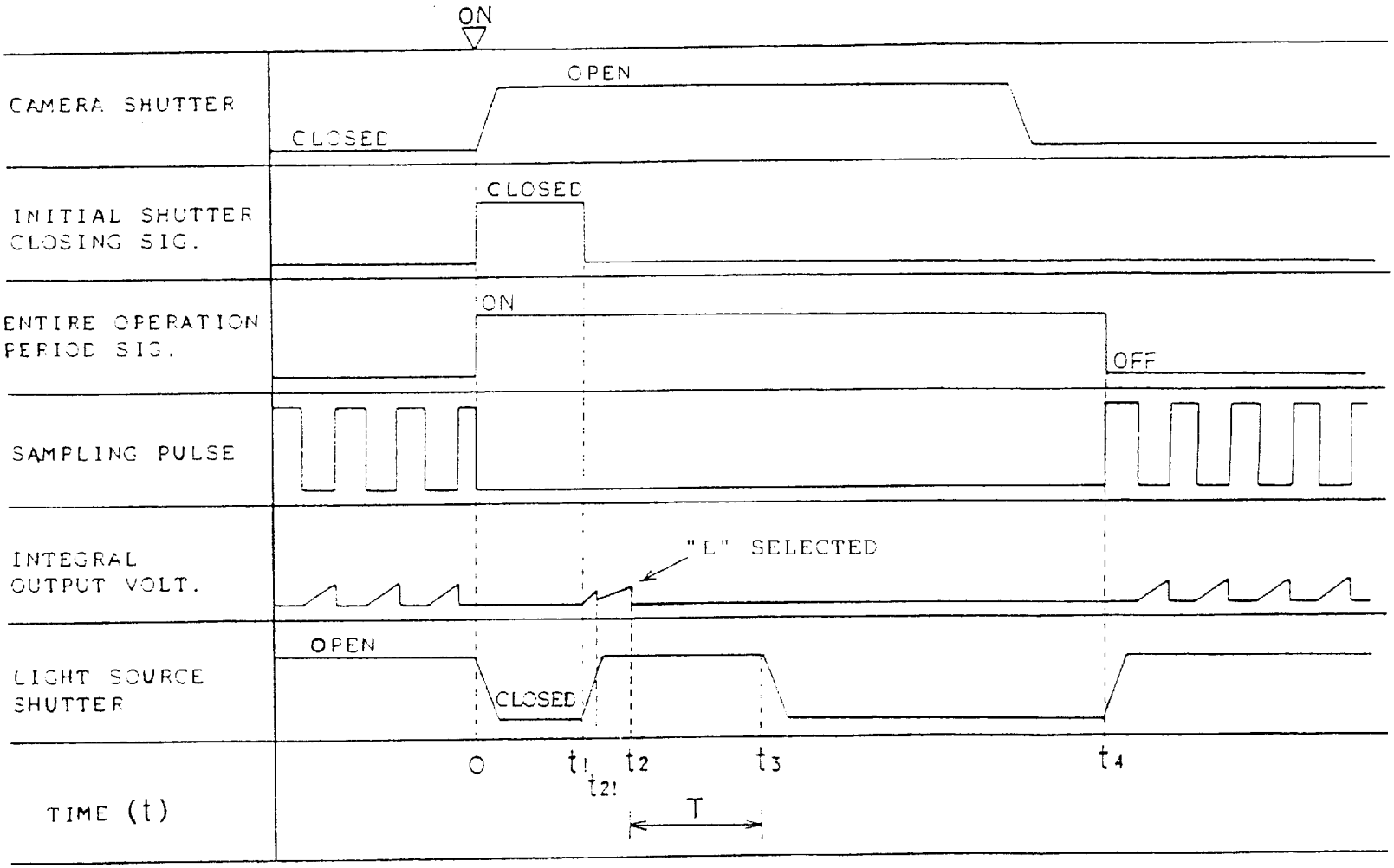
FIG. 8 is a time chart showing the operation of the second embodiment.

FIG. 8 shows an arrangement in which the integral output voltage V is inputted immediately after the light source shutter 42 is opened (e.g., from 0.001 to 0.002 sec after it), i.e., at $t_{21}$, and either the output L from the second amplifier 72 or the output H from the third amplifier 73 is selected in accordance with the input value.

However, the integral output voltage V at $t_{21}$ is not employed for calculation of dV/dt. This is because the integral output voltage V, at this point of time is very small and hence influenced greatly by the noise or by the fluctuation of the motion of the light source shutter 42.

Accordingly, the calculation of dV/dt is performed when the time $t_2$ has elapsed since the turning on of the synchro switch 21, and the remaining exposure time T is calculated at that time.

Figure 9:
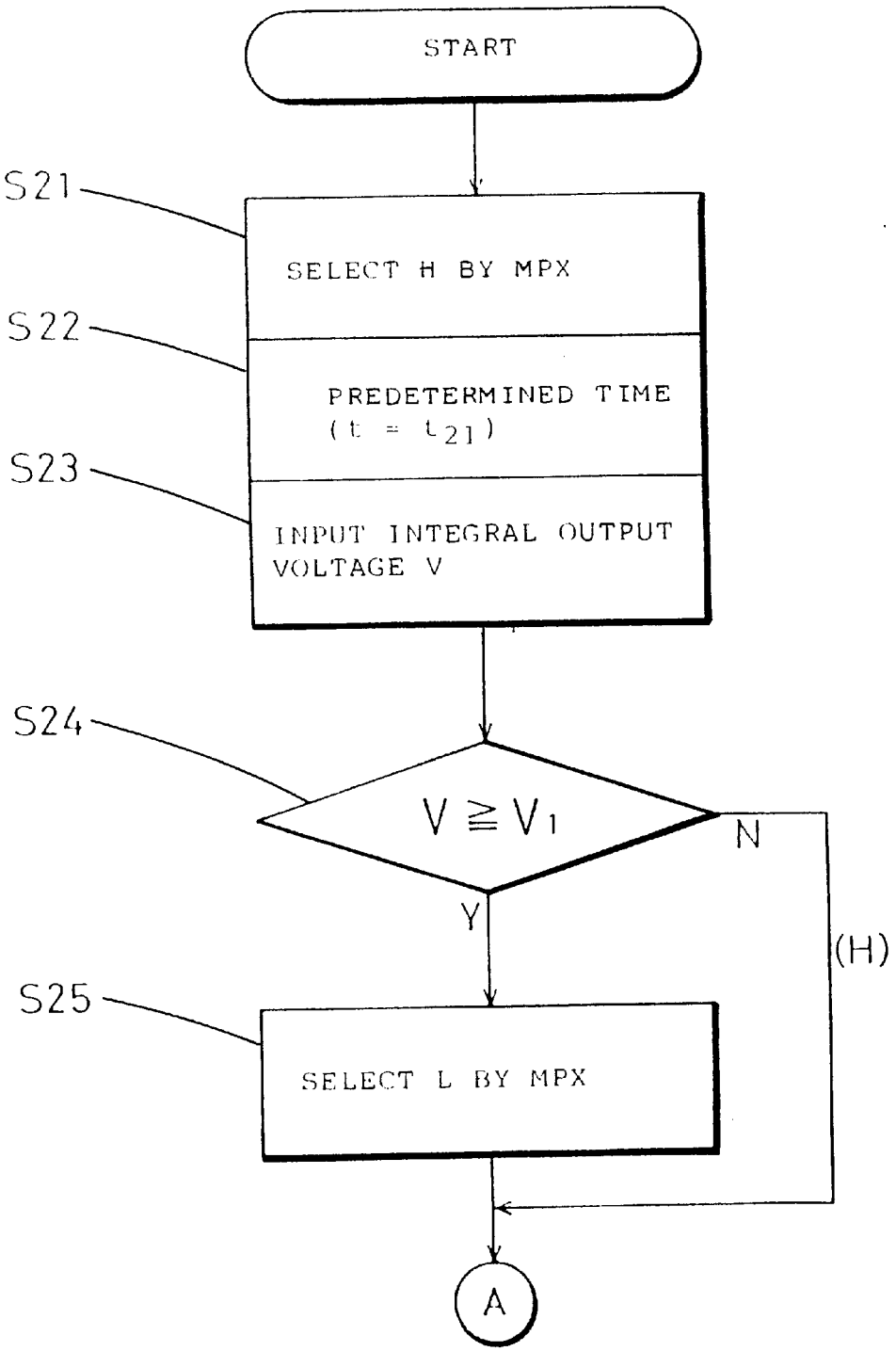
FIG. 9 is a flowchart showing a control process in the second embodiment.

FIG. 9 is a flowchart showing a process for executing the above-described operation. In this case, when the synchro switch 21 is turned on, the output H from the third amplifier 73 is first selected in the multiplexer 61 at S21. Next, after a predetermined time $t_{21}$ has elapsed at S22, the integral output voltage V is inputted at S23.

Then, if the integral output voltage V is equal to or greater than a reference value $V_1$ at S24, the output L from the second amplifier 72 is selected in the multiplexer 61 at S25, whereas, if the integral output voltage V is smaller than the reference value $V_1$ at S24, the output H from the third amplifier 73 is left in the selected state. Thereafter, the process proceeds to S4 in FIG. 7.

Figure 10:
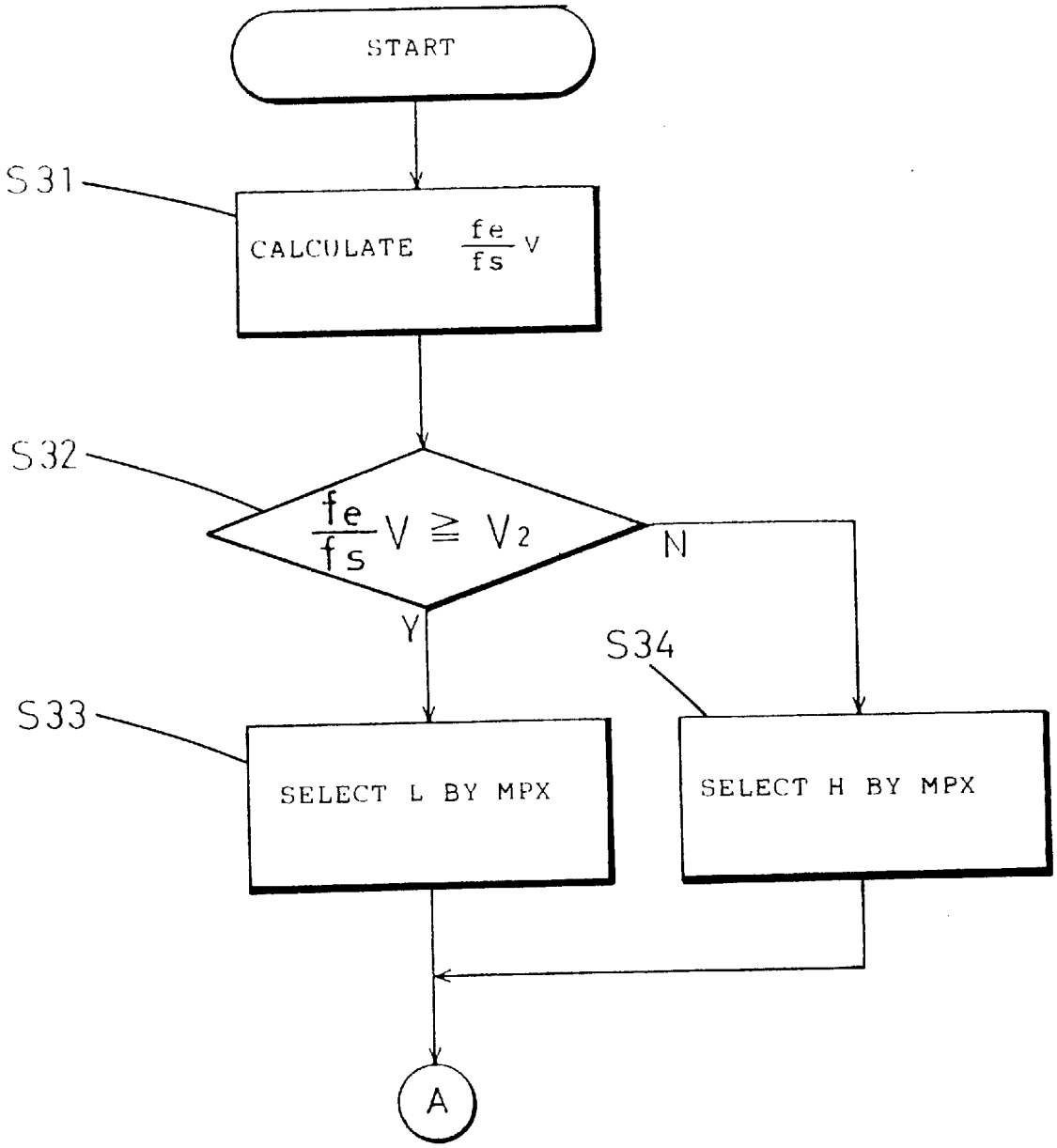
FIG. 10 is a flowchart showing a control process in the third embodiment.

FIG. 10 is a flowchart showing a control process wherein the selection of an amplifier is effected on the basis of the integral output voltage V that is obtained in response to the sampling pulse during the normal observation. In this case, when the synchro switch 21 is turned on, V·fe/fs is calculated at S31. In the expression, fe is the aperture of the diaphragm 43 during photographing, and fs is the aperture of the diaphragm 43 immediately before photographing is initiated.

Next, if V·fe/fs is equal to or greater than a reference value $V_2$ at S32, the output L from the second amplifier 72 is selected in the multiplexer 61 at S33. Conversely, if V·fe/fs is smaller than the reference value $V_2$ at S32, the output H from the third amplifier 73 is selected in the multiplexer 61 at S34. Thereafter, the process proceeds to S4 in FIG. 7.

In the foregoing embodiments, dV/dt is obtained to calculate the remaining predicted exposure time T, and when the exposure time T has elapsed, the light source shutter 42 is closed.

Figure 11:
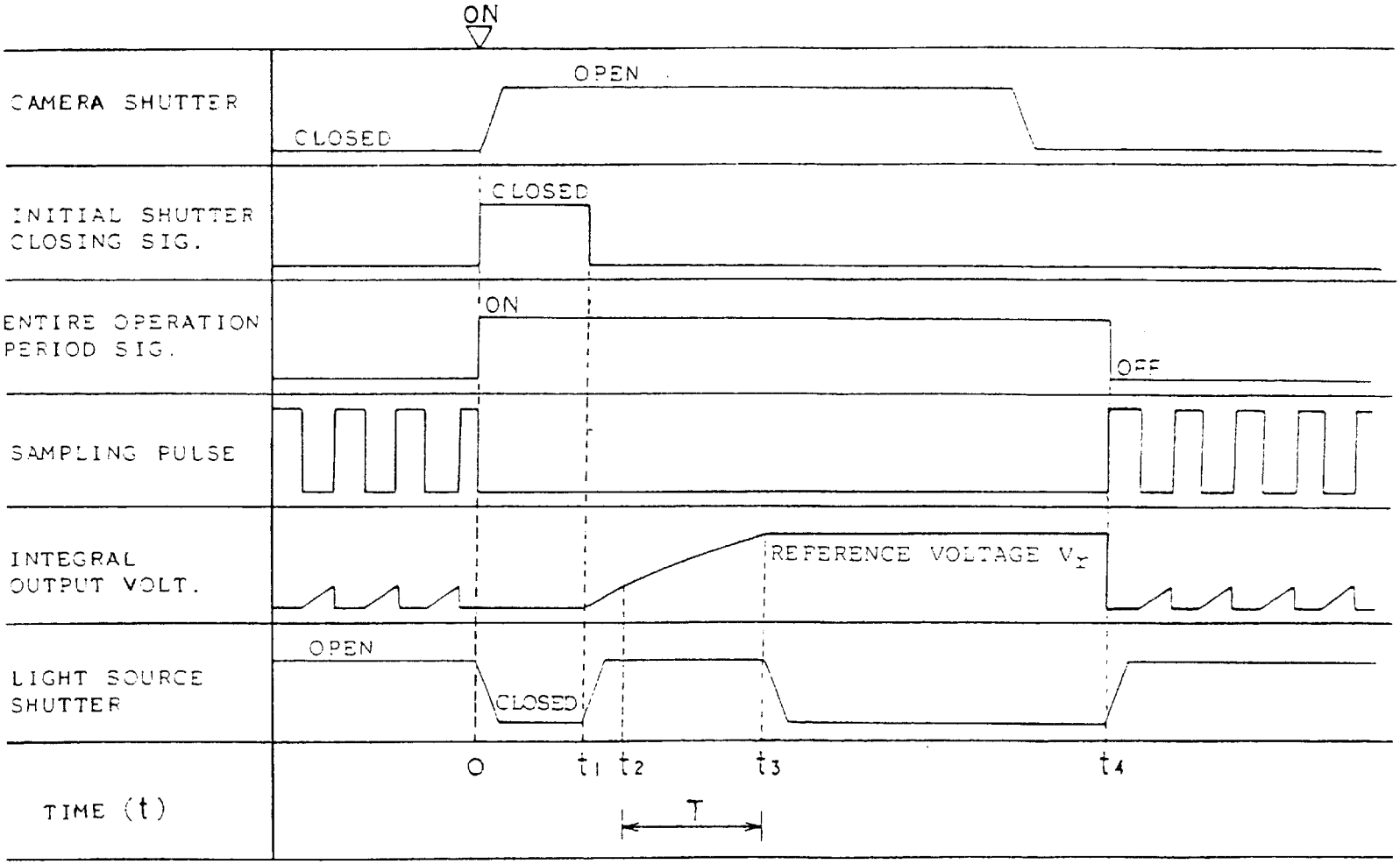
FIG. 11 is a time chart showing the operation of the fourth embodiment.

In the following embodiment, the integral output voltage V is constantly monitored after the light source shutter 42 is opened, and when the voltage value reaches a reference voltage Vr. Also the light source shutter 42 is closed to terminate the exposure operation, as shown in FIG. 11, thereby effecting even more careful control.

In this case, when dV/dt is obtained after the time $t_2$ has elapsed since the turning on of the synchro switch 21, the output H from the third amplifier 73 is selected, thereby accurately obtaining dV/dt within a short period of time. Thereafter, the output L from the second amplifier 72 is selected to prevent breakage of the electronic elements due to an excess voltage.

It should be noted that the time $t_2$ in the above-described embodiments need not be coincident with each other.

Figure 12:
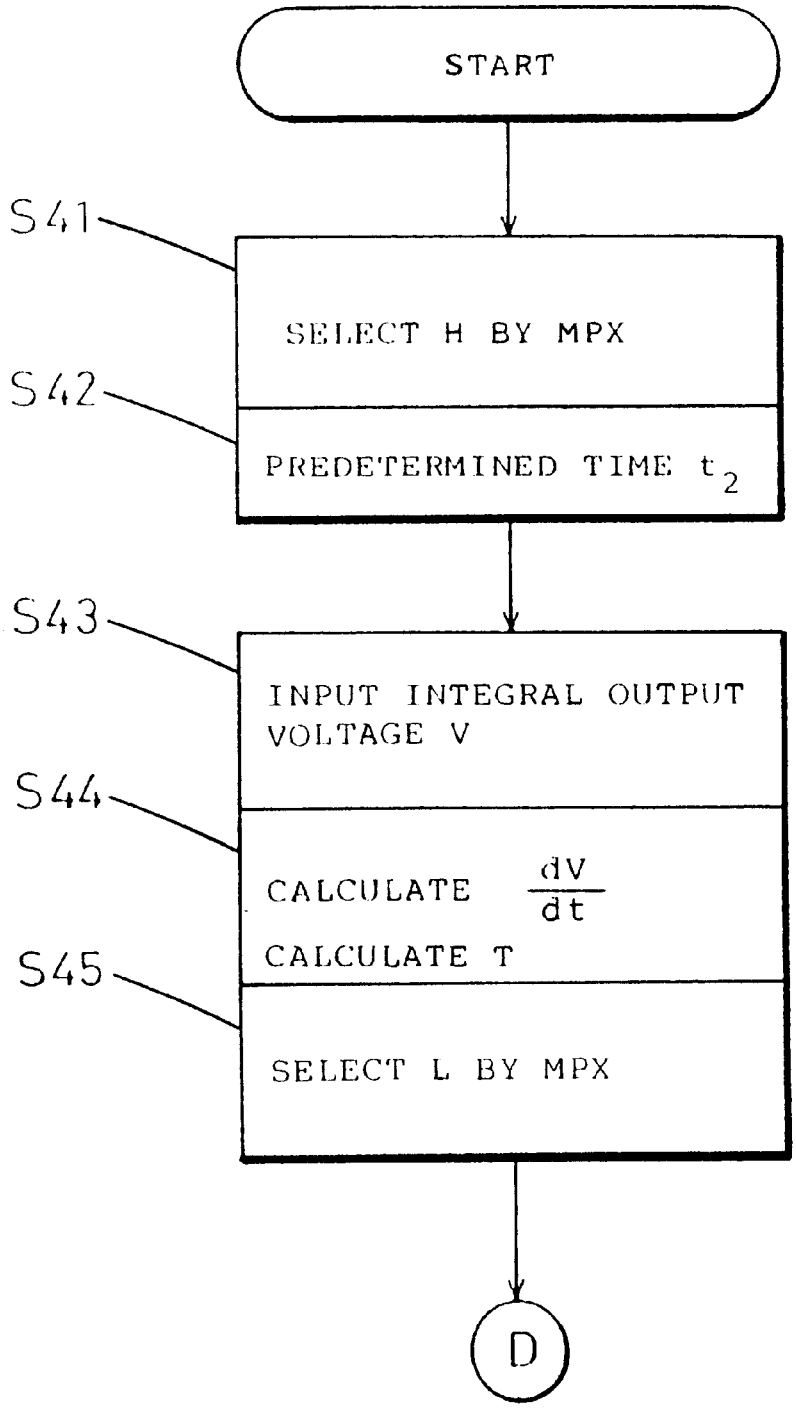
FIGS. 12 and 13 are flowcharts showing a control process in the fourth embodiment.
Figure 13:
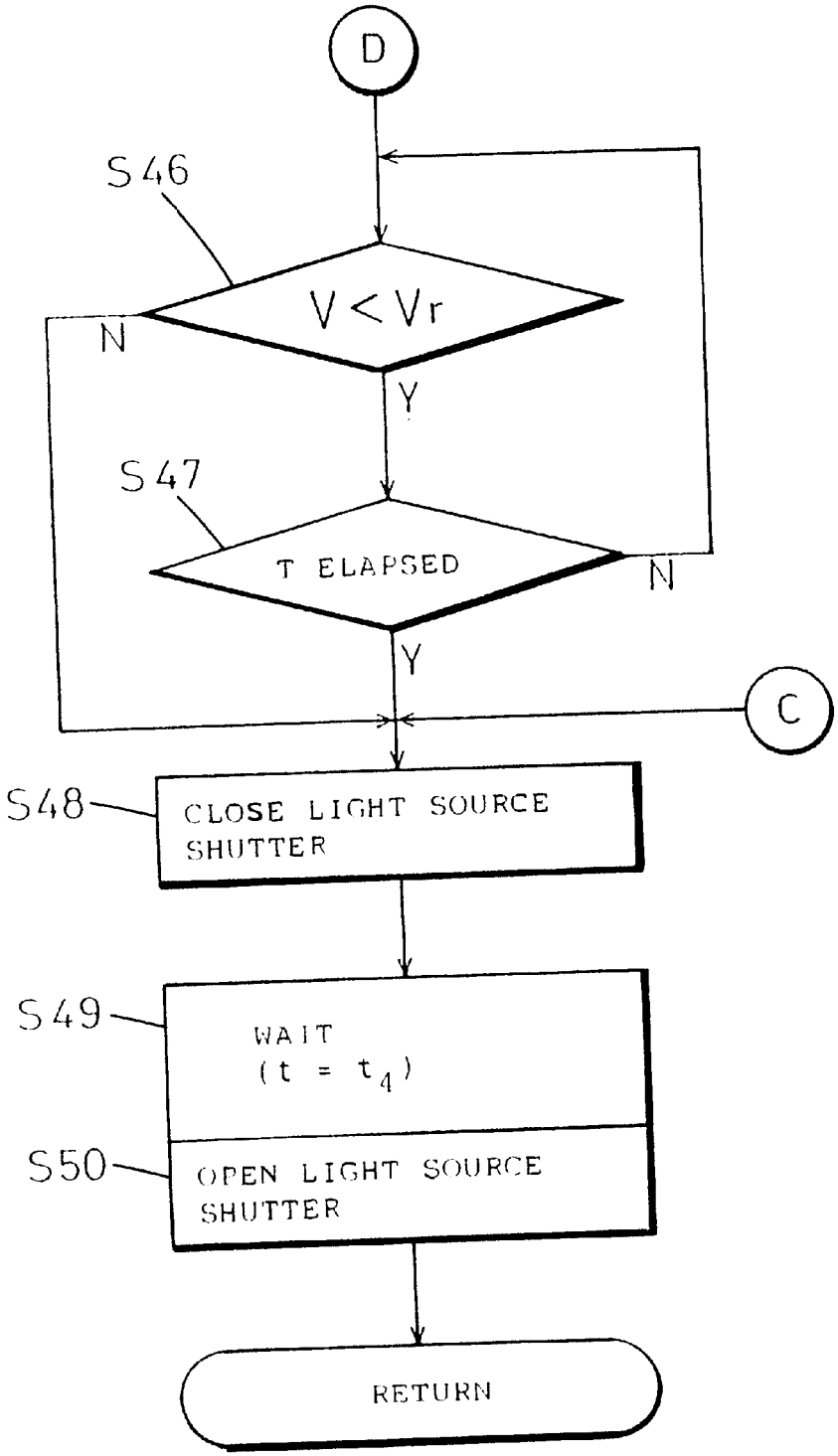

FIGS. 12 and 13 are flowcharts showing the above-described control process.

When the synchro switch 21 is turned on, the output H from the third amplifier 73 is selected in the multiplexer 61 at S41, and then the elapse of the time $t_2$ is awaited at S42.

When the time $t_2$ has elapsed, the integral output voltage V is inputted at S43, and dV/dt and T are calculated at S44. Then, the output L from the second amplifier 72 is selected at S45.

When the integral output voltage V reaches a reference voltage Vr at S46 or the predicted exposure time T has elapsed at S47, the light source shutter 42 is closed at S48.

Next, the elapse of the entire operation terminating time $t_4$ is awaited at S49, and the light source shutter 42 is then opened at S50 to return to the normal observation state.

Figure 14:
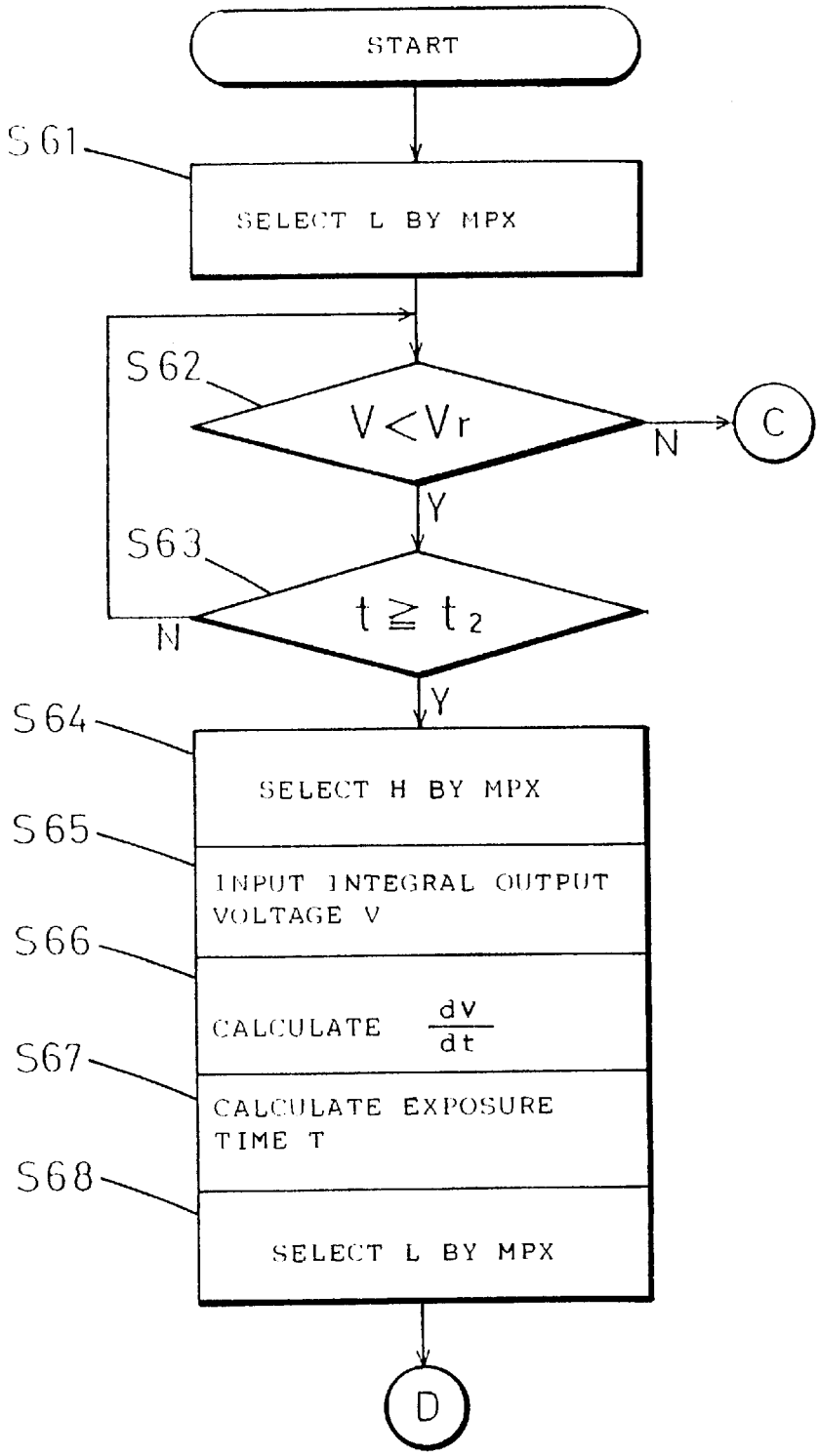
FIG. 14 is a flowchart showing a control process in the fifth embodiment.

FIG. 14 is a flowchart showing a control process that takes into consideration a case where the integral output voltage V reaches the reference voltage Vr before the elapse of the time $t_2$ for obtaining dV/dt.

In this process, when the synchro switch 21 is turned on, the output L from the second amplifier 72 is selected in the multiplexer 61 at S61. If it is decided at S62 and S63 that the integral output voltage V reaches the reference voltage Vr before the time $t_2$ has elapsed, the process proceeds to S48 in FIG. 13 to close the light source shutter 42.

If it is decided at S62 and S63 that the integral output voltage V has not yet reached the reference voltage Vr when the time $t_2$ has elapsed, the output H from the third amplifier 73 is selected in the multiplexer 61 at S64, and the integral output voltage V is inputted at S65.

Then, dV/dt is calculated at S66, the remaining predicted exposure time T is calculated at S67, and the output L from the second amplifier 72 is selected in the multiplexer 61 at S68. Thereafter, the process proceeds to S46 in the FIG. 13.

Although the foregoing embodiments employ two different kinds of amplifier which are selected after the synchro switch 21 is turned on, it should be noted that the number of such amplifiers may be increased to effect even more delicate control.

In addition, the amplification factor H need not be fixed. For example, H may be selected from among a plurality of amplification factors in a similar manner to that in the embodiments shown in FIGS. 1 to 11.

According to the present invention, the amplification factor for the integral output voltage is automatically switched over from one to another in accordance with the brightness of the object. Accordingly, it is possible to obtain a signal with a proper level independently of the brightness of the object and hence possible to effect accurate photographing light quantity control. Thus, photographing of high quality can be performed.

While the invention has been described by reference to specific embodiments chosen for purposes of illustration, it should be apparent that numerous modifications could be made thereto by those skilled in the art without departing from the basic concept and scope of the invention.

We claim:

1. A photographing light quantity controller for an endoscope, which is used to control a quantity of illuminating light when a photograph is to be taken through said endoscope, comprising:

means for supplying light for illuminating an object to said endoscope;

means for detecting a quantity of light that is reflected from said object and for outputting a signal in accordance with the detected quantity of light;

means for amplifying said signal, said amplifying means having a plurality of amplification factors which can be selected as desired;

photographing light [quality] *quantity* control means for controlling the quantity of illuminating light that is supplied to said endoscope when a photographing operation is conducted, on a basis of the output signal from said amplifying means; and means for automatically switching over said amplification factors of said amplifying means from one to another in accordance with a brightness of said object.

2. A photographing light quantity controller for an endoscope, which is used to control a quantity of illuminating light when a photograph is to be taken through said endoscope, comprising:

means for supplying light for illuminating an object to said endoscope;

a device for photographing said object;

photoelectric conversion means for converting a brightness level of light, that is reflected from said object, into an electric signal;

means for integrating an output from said photoelectric conversion means and outputting a resulting integral value;

means for amplifying the output value from said integrating means, said amplifying means having a plurality of amplification factors which can be selected as desired;

photographing light quality control means for controlling the quantity of illuminating light that is supplied to said endoscope when a photographing operation is conducted, on a basis of the output signal from said amplifying means;

a switch for initiating said photographing operation of said photographing device *and* said control operation of said photographing light quantity control means; and means for automatically switching over said amplification factors of said amplifying means from one to another in accordance with a brightness of said object.

3. A photographing light quantity controller for an endoscope according to claim 2, wherein said amplifying means has a plurality of amplifiers with different amplification factors.

4. A photographing light quantity controller for an endoscope according to claim 2, wherein said amplification factors are switched over in such a manner that, when the output value from said integrating means is small, an amplification factor switching means selects a large amplification factor from among said plurality of amplification factors of said amplifying means, whereas, when the output value from said integrating means is large, said amplification factor switching means selects a small amplification factor from among said plurality of amplification factors.

5. A photographing light quantity controller for an endoscope according to claim 4, wherein said amplification factors switching means switches over said amplification factors from one to another after said switch is turned on.

6. A photographing light quantity controller for an endoscope according to claim 4, wherein said amplification factor switching means switches over said amplification factors from one to another before said switch is turned on.

7. A photographing light quantity controller for an endoscope according to claim 2, wherein said integrating means integrates the output from said photoelectric conversion means for a period of time which is shorter than an exposure time immediately after exposure has been initiated, at least with respect to a photographing plane in said photographing device.

8. A photographing light quantity controller for an endoscope according to claim 2, wherein said photographing light quantity control means obtains a rate of change of the output value from said amplifying means per unit time and controls the quantity of illuminating light for photographing on a basis of the value obtained.

9. A photographing light quantity controller for an endoscope according to claim 8, wherein said photographing light quantity control means calculates remaining exposure time required to obtain the quantity of illuminating light for photographing from said rate of change of the output value from said amplifying means per unit time and terminates the supply of the illuminating light to said endoscope after said remaining exposure time has elapsed.

10. A photographing light quantity controller for an endoscope according to claim 8, wherein said photographing light quantity control means terminates the supply of the illuminating light to said endoscope when the output value from said amplifying means reaches a predetermined value.

11. A photographing light quantity controller for an endoscope according to claim 5, wherein said amplification factor switching means selects one said amplification factors on the basis of the output value from said amplifying means that is delivered a short time after said switch is turned on.

12. A photographing light quantity controller for an endoscope according to claim 11, wherein said photographing light quantity control means controls the quantity of illuminating light for photographing on a basis of a rate of change of the output value from said amplifying means per unit time after an amplification factor is selected by said amplification factor switching means.

13. A photographing light quantity controller for an endoscope according to claim 12, wherein said amplification factor of said amplifying means, this is employed when said photographing light quantity control means controls the quantity of illuminating light, is not larger than said amplification factor of said amplifying means that is employed when said amplification factor switching means selects said amplification factor.

14. A photographing light quantity controller for an endoscope according to claim 2, further comprising means for making a comparison between the integral value, outputted from said integrating means after said switch has been turned on, and a preset reference value, and for terminating the supply of the illuminating light to said endoscope when said integral value reaches said reference value.

*15. A method for controlling a quantity of photographing light for an endoscope when a photograph of an object is taken through said endoscope during a photographing operation, the method comprising:*

*supplying light for the illumination of said object to said endoscope by an illuminating device;*

*detecting a quantity of light reflected by said object;*

*generating a light quantity signal corresponding to said quantity of light;*

*integrating said light quantity signal and emitting a resultant integral value;*

*controlling said quantity of photographing light which is supplied to said endoscope when carrying out a photographing operation depending on said integral value;*

*calculating, after a first period of time after the beginning of exposure, a remaining exposure time from said resultant integral value in the photographing operation; and*

*amplifying said resultant integral value by a first amplification factor during said first time period, and a second amplification factor during the remaining exposure time after calculation of the remaining exposure time.*

*16. The method according to claim 15, wherein said first amplification factor is higher than said second amplification factor.*

*17. The method according to claim 15, further comprising amplifying said resultant integral value by a third amplification factor before said first period of time, said third amplification factor being lower than said first amplification factor.*

*18. The method of claim 15, comprising converting a brightness level of said light reflected by said object into an electric signal and calculating said remaining exposure time for reaching the required quantity of photographing light from an increase of the resultant integral value amplified per unit time.*

*19. The method according to claim 15, further comprising:*

*comparing said resultant integral value with a reference value during the duration of exposure; and*

*stopping said exposure upon a first occurrence of one of said remaining exposure time elapsing and said resultant integral value reaching said reference value.*

*20. A photographing light quantity controller for an endoscope which is used to control a quantity of illuminating light when a photograph is to be taken through said endoscope, comprising:*

*means for supplying light for illuminating an object to said endoscope;*

*means for detecting a quantity of light that is reflected from said object and for outputting a signal in accordance with the detected quantity of light;*

*a device for integrating said light quantity signal outputted by said detecting means and for emitting a resulting integral value, said resultant integral value being an integral output voltage;*

*photographing light quantity control means for controlling the quantity of illuminating light that is supplied to said endoscope when a photographing operation is conducted, depending on said resultant integral value;*

*a device for calculating a remaining exposure time from said resultant integral value after a first period of time after a beginning of exposure in the photographing operation; and*

*an amplifying system that amplifies said resultant integral value by a first amplification factor during said first time period, and by a second amplification factor during the remaining exposure time after calculation of the remaining exposure time.*

*21. A photographing light quantity controller for an endoscope according to claim 15, wherein said amplifying system is operable using a plurality of amplification factors, and including a device that automatically switches over said plurality of amplification factors of said amplifying system so that said resultant integral value is amplified by said first amplification factor during said first period of time and by said second amplification factor during said remaining exposure time after calculation of said remaining exposure time.*

*22. A photographing light quantity controller for an endoscope according to claim 20, wherein said amplifying system comprises a plurality of amplifiers having different amplification factors.*

*23. A photographing light quantity controller for an endoscope according to claim 20, wherein said means for detecting comprises a photoelectric conversion device for converting a brightness level of the light reflected by said object into an electric signal; and*

*wherein said device for calculating a remaining exposure time further comprises a device for forming a derivation of said resultant integral value to be used in calculating said remaining exposure time.*

*24. A photographing light quantity controller for an endoscope according to claim 20, further comprising a light source shutter adjacent said means for supplying light, said exposure being stopped by closing said light source shutter.*

*25. A photographing light quantity controller for an endoscope according to claim 20, wherein said amplifying system is operable using a plurality of amplification factors, and including a device that automatically switches over said plurality of amplification factors of said amplifying system so that said resultant integral value is amplified by said first amplification factor during said first period of time, by another amplification factor after said first period of time and before said remaining exposure time is calculated, and by said first amplification factor after calculation of said remaining exposure time.*

*26. A photographing light quantity controller for an endoscope according to claim 20, further comprising:*

*a comparing device for comparing said resultant integral value with a predetermined reference value; and*

*means for stopping said exposure upon a first occurrence of one of said integral output voltage value reaching said predetermined reference value and said remaining exposure time elapsing.*

* * * * *